US006500133B2

(12) United States Patent
Martin et al.

(10) Patent No.: US 6,500,133 B2
(45) Date of Patent: Dec. 31, 2002

(54) APPARATUS AND METHOD FOR PRODUCING HIGH INTENSITY FOCUSED ULTRASONIC ENERGY FOR MEDICAL APPLICATIONS

(75) Inventors: Roy W. Martin, Seattle, WA (US); Mark D. Brentnall, San Diego, CA (US); Andrew H. Proctor, Duvall, WA (US)

(73) Assignee: University of Washington, Seattle, WA (US)

( * ) Notice: Subject to any disclaimer, the term of this patent is extended or adjusted under 35 U.S.C. 154(b) by 138 days.

(21) Appl. No.: 09/728,100

(22) Filed: Dec. 1, 2000

(65) Prior Publication Data

US 2001/0014780 A1 Aug. 16, 2001

Related U.S. Application Data

(62) Division of application No. 09/312,745, filed on May 14, 1999, now Pat. No. 6,217,530.

(51) Int. Cl.[7] .................................................. A61N 7/02
(52) U.S. Cl. .......................................... 601/3; 310/335
(58) Field of Search ........................ 601/2, 3; 600/439, 600/459; 310/335, 311, 367, 348, 371, 349; 606/27; 604/22

(56) References Cited

U.S. PATENT DOCUMENTS

| | | | | |
|---|---|---|---|---|
| 4,184,094 A | * | 1/1980 | Kopel | 310/335 |
| 4,435,985 A | * | 3/1984 | Wickramasinghe | 73/642 |
| 4,475,376 A | * | 10/1984 | Keilman | 73/1.86 |
| 4,743,870 A | * | 5/1988 | Jen et al. | 333/147 |
| 4,787,070 A | * | 11/1988 | Suzuki et al. | 367/140 |
| 4,899,757 A | * | 2/1990 | Pope, Jr. et al. | 600/463 |
| 5,235,553 A | * | 8/1993 | Garlick et al. | 367/7 |
| 5,522,878 A | * | 6/1996 | Montecalvo et al. | 607/152 |
| 5,577,507 A | * | 11/1996 | Snyder et al. | 600/472 |
| 5,738,098 A | * | 4/1998 | Brock-Fisher et al. | 600/472 |
| 6,007,499 A | * | 12/1999 | Martin et al. | 601/3 |
| 6,113,559 A | * | 9/2000 | Klopotek | 601/3 |
| 6,206,843 B1 | * | 3/2001 | Iger et al. | 601/2 |
| 6,217,530 B1 | * | 4/2001 | Martin et al. | 601/2 |
| 6,234,990 B1 | * | 5/2001 | Rowe et al. | 604/22 |

* cited by examiner

Primary Examiner—Shawna J Shaw
(74) Attorney, Agent, or Firm—Eugene H. Valet

(57) ABSTRACT

A medical instrument uses solid tapered cones mounted to a preferably concave, spherically curved, piezoelectric ultrasound transducer which focuses and concentrates the ultrasound energy to a narrow tip so very high levels of ultrasound can be delivered to the tissue adjacent to the tip. Ultrasound matching layers or variable curvature geometries are employed at the tip aid in transferring the energy from the tip to the tissue.

14 Claims, 13 Drawing Sheets

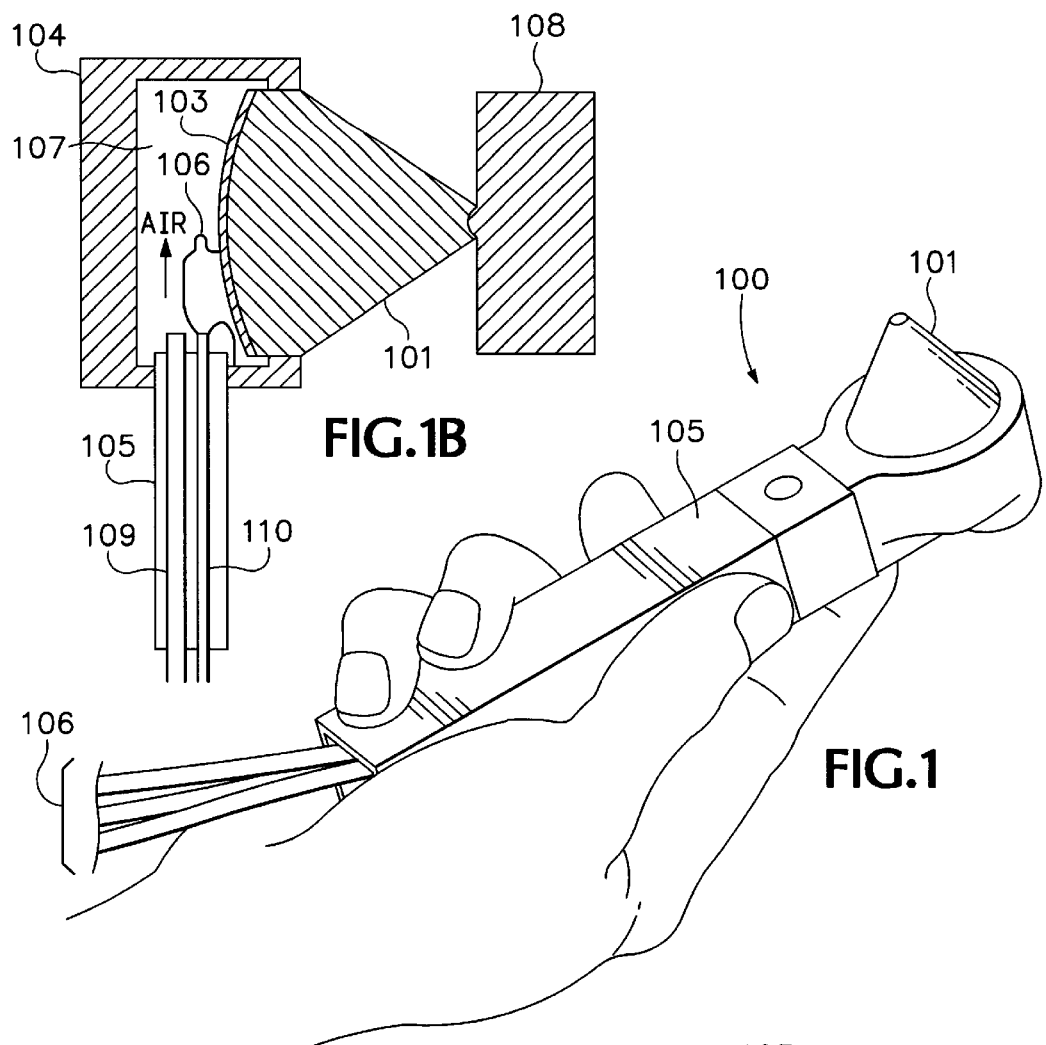
FIG.1B
FIG.1
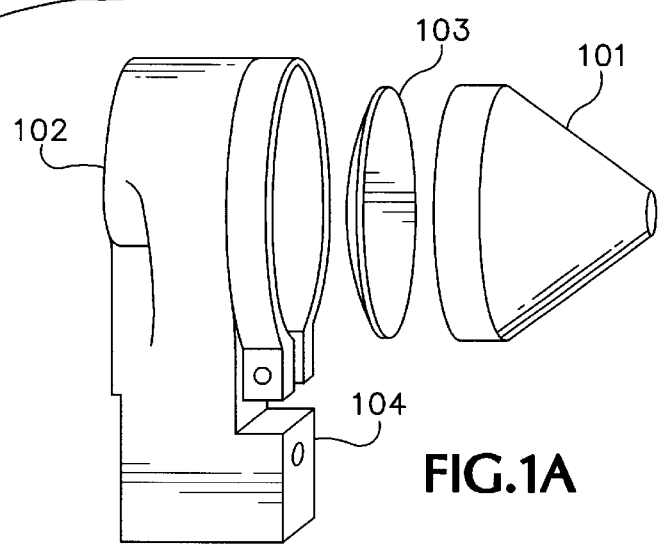
FIG.1A

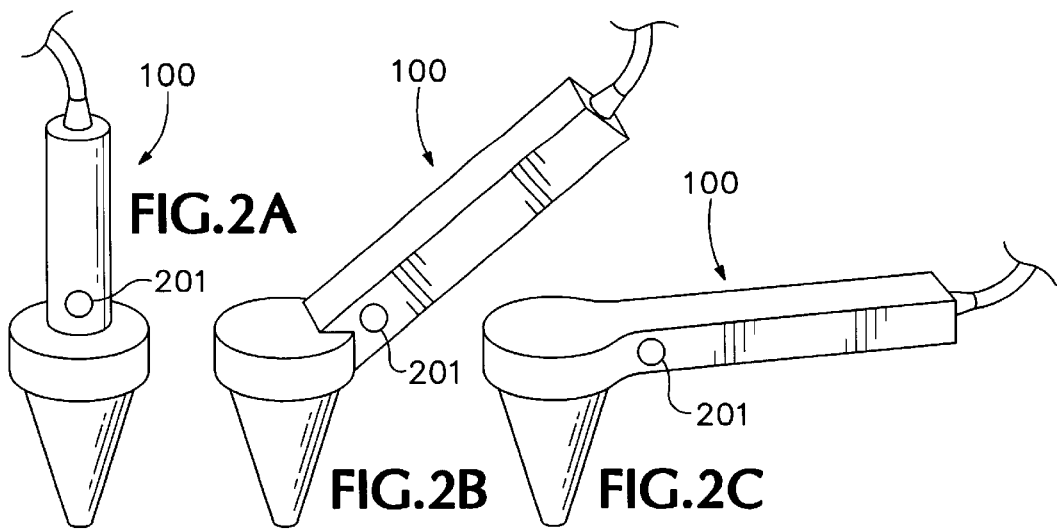
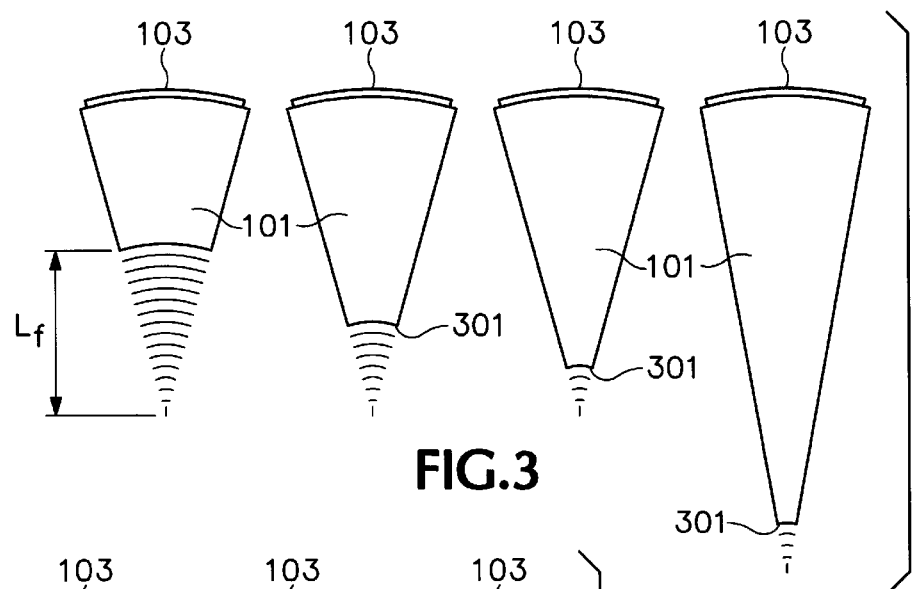
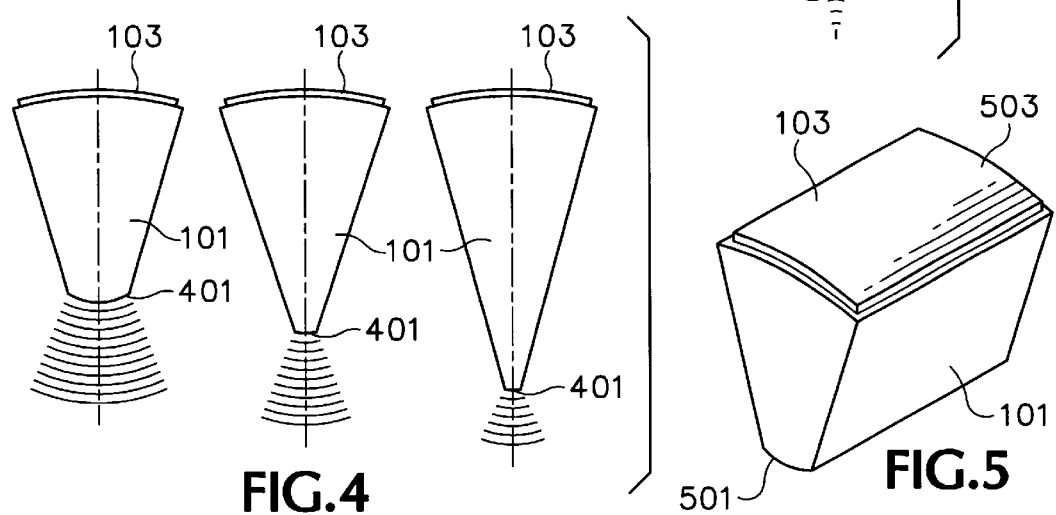

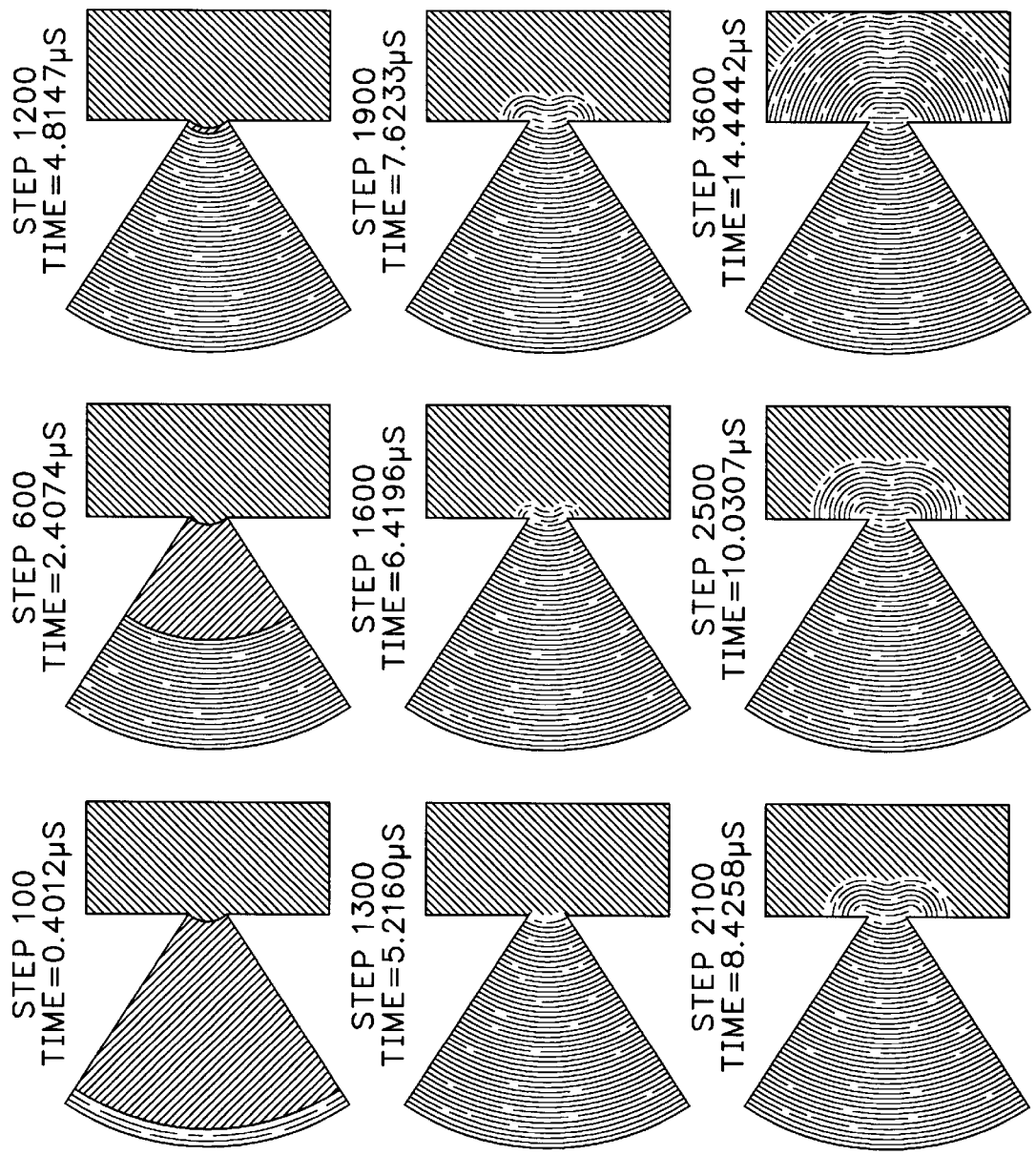

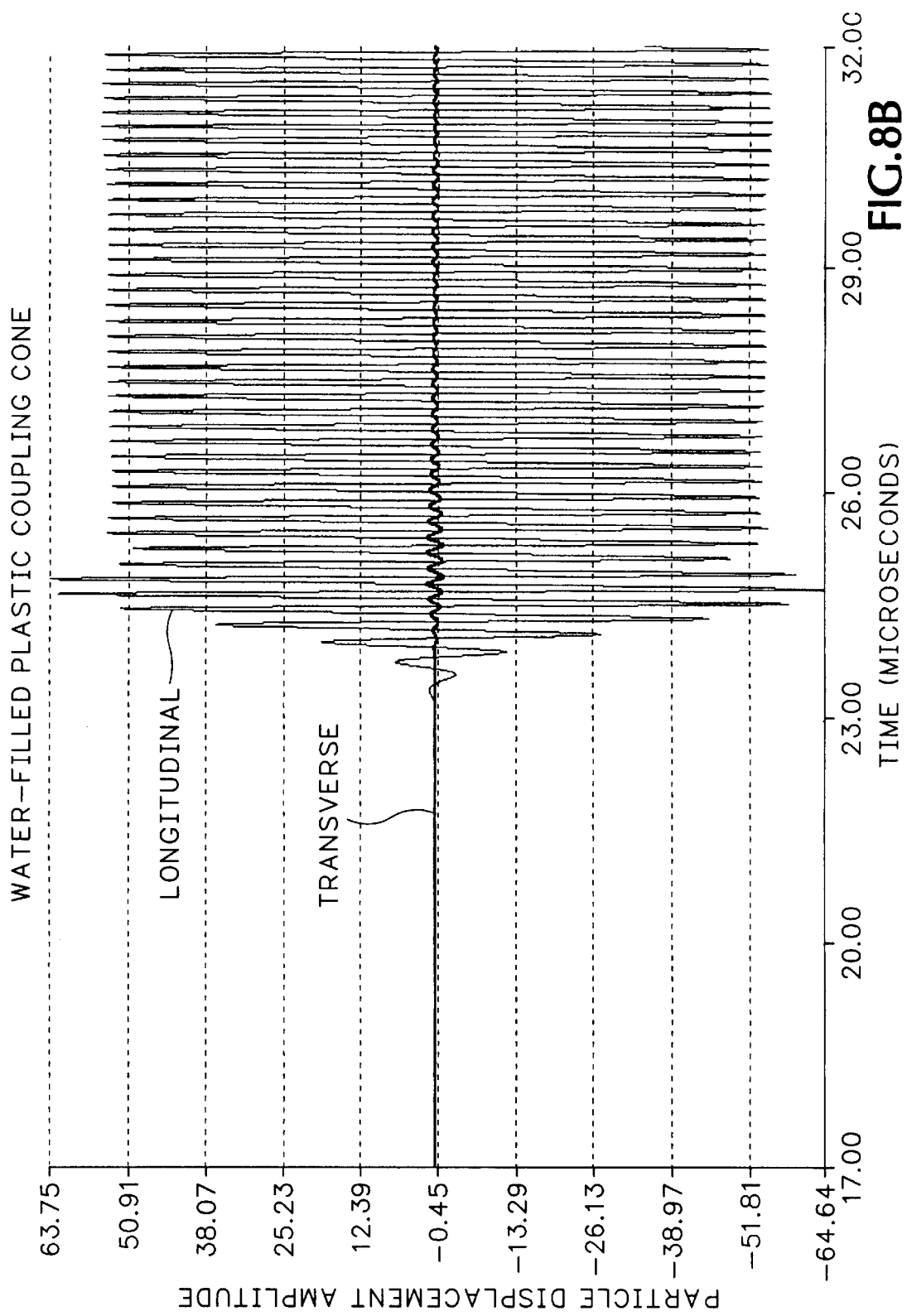

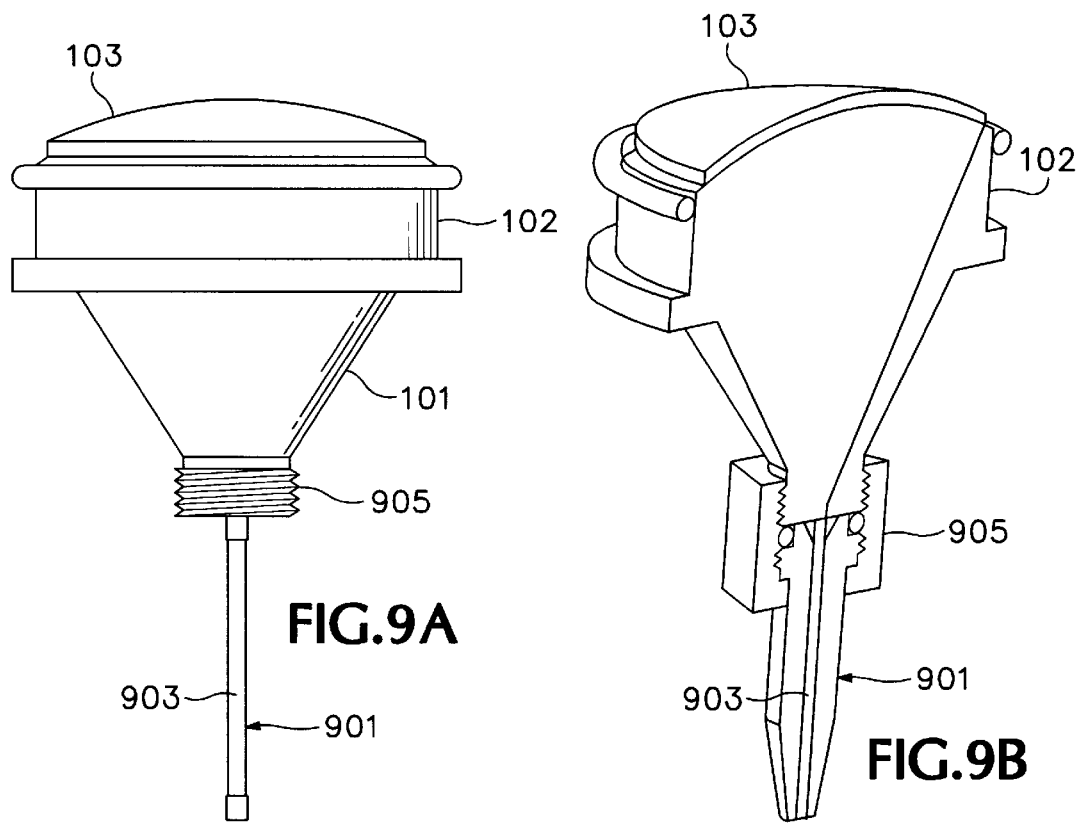
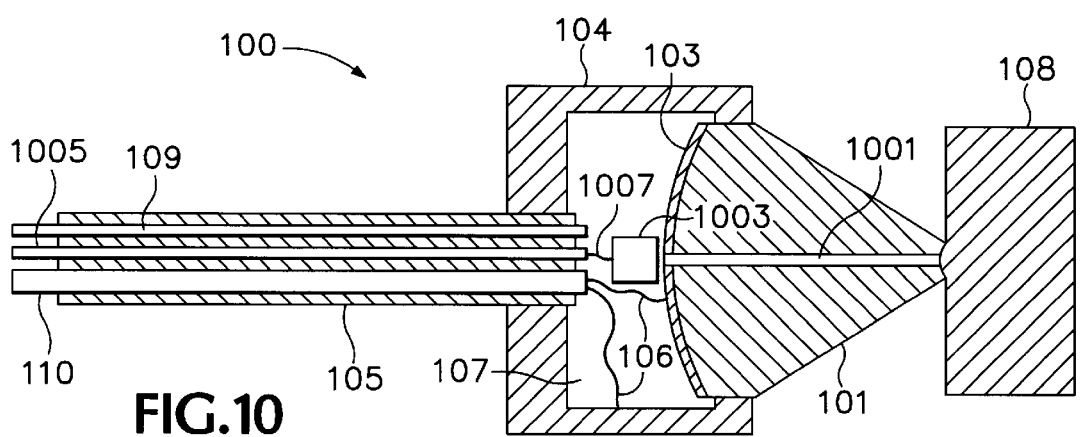

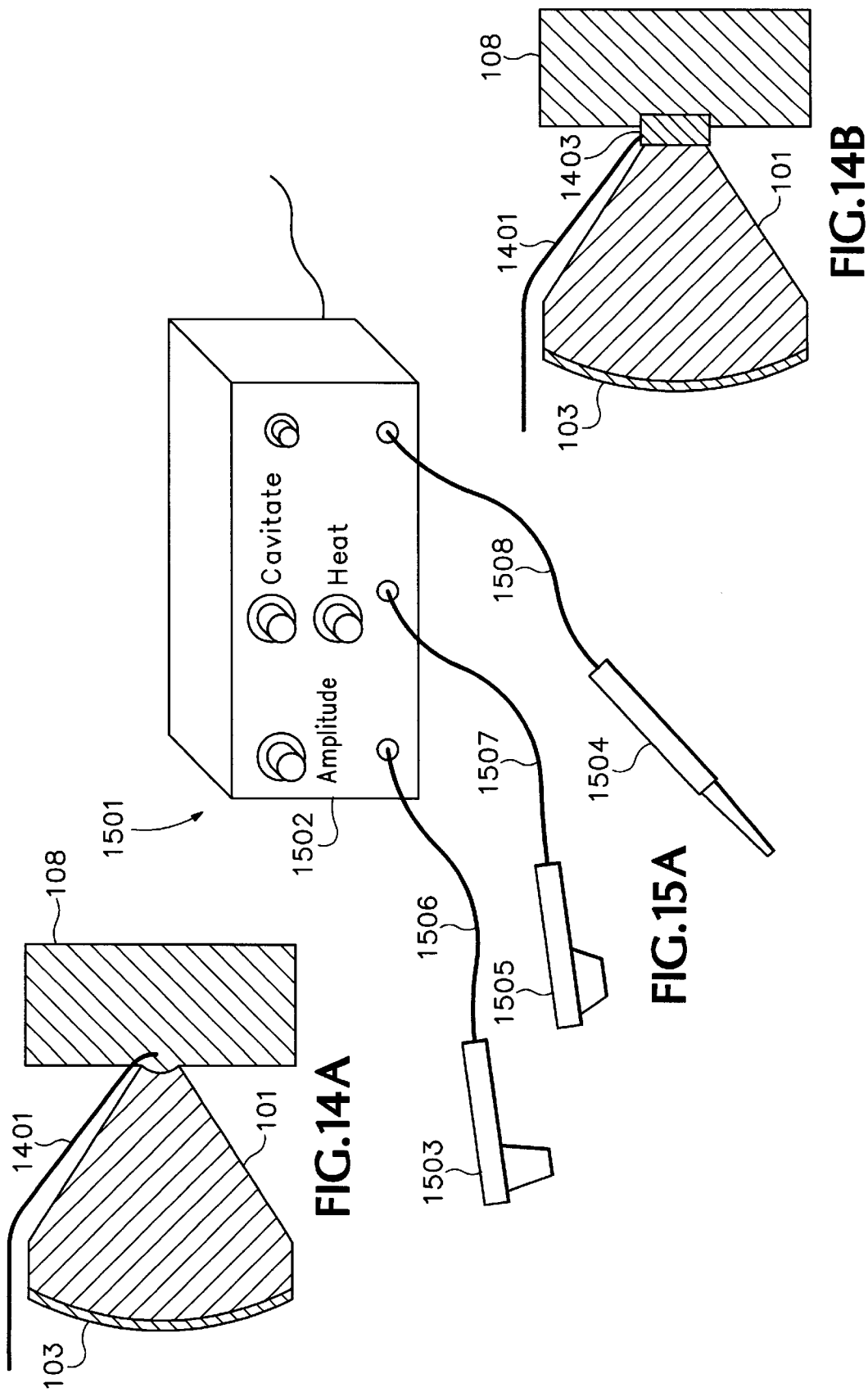

APPARATUS AND METHOD FOR PRODUCING HIGH INTENSITY FOCUSED ULTRASONIC ENERGY FOR MEDICAL APPLICATIONS

This is a divisional of U.S. patent application Ser. No. 09/312,745 filed May 14, 1999 now U.S. Pat. No. 6,217,530 issued Apr. 17, 2001.

The invention described herein was made in the course of work under a grant or award from the U.S. Department of Defense, Office of Naval Research.

BACKGROUND OF THE INVENTION

1. Field of the Invention

The present invention relates generally to methods and apparatus using ultrasonics in the field of medical technology and, more particularly, to an applicator for performing presurgical and surgical procedures using high-intensity focused ultrasound.

2. Description of Related Art

Therapeutic ultrasound refers to the use of high intensity ultrasonic waves to induce changes in living tissue state through both thermal effects—referred to in the art as induced hyperthermia—and mechanical effects—induced cavitation. High frequency ultrasound has been employed in both hyperthermic and cavitational medical applications, whereas low frequency ultrasound has been used principally for its cavitation effect. Diagnostic medical ultrasonic imaging is well known, for example, in the common use of sonograms for fetal examination. Various aspects of diagnostic and therapeutic ultrasound methodologies and apparatus are discussed in depth in an article by G. ter Haar, *Ultrasound Focal Beam Surgery*, Ultrasound in Med. & Biol., Vol. 21, No. 9, pp. 1089–1100, 1995, and the *IEEE Transactions on Ultrasonics, Ferroelectrics, and Frequency Control*, November. 1996, Vol. 43, No. 6 (ISSN 0885-3010), incorporated herein by reference. Particular methods and apparatus for medical applications of high intensity focused ultrasound, for example, for hemostasis and tissue necrotization, are the subject of pending U.S. patent application Ser. No. 08/961,972 now U.S. Pat. No. 6,007,499 issued Dec. 28, 1999 (assigned to the common assignee of the present invention and incorporated herein by reference).

In high-intensity focused ultrasound (HIFU) hyperthermia treatments, intensity of ultrasonic waves generated by a highly focused transducer increases from the source to the region of focus, or focal region, where it can cause a high temperature effect, e.g. to 98° Centigrade. The absorption of the ultrasonic energy at the focus induces a sudden temperature rise of targeted tissue—as high as one to two hundred degrees Kelvin/second—which causes the irreversible ablation of the target volume of cells. Thus, for example, HIFU hyperthermia treatments can cause necrotization of or around an internal lesion without damage to the intermediate tissues. The focal region dimensions are referred to as the depth of field, and the distance from the transducer to the center point of the focal region is referred to as the depth of focus. In the main, ultrasound is a promising non-invasive surgical technique because the ultrasonic waves provide a non-effective penetration of intervening tissues, yet with sufficiently low attenuation to deliver energy to a small focal target volume. Currently there is no other known modality that offers noninvasive, deep, localized focusing of non-ionizing radiation for therapeutic purposes. Thus, ultrasonic treatment has a great advantage over microwave and radioactive therapeutic treatment techniques.

Blood loss due to internal or external bleeding in trauma patients and hemorrhage in surgery is a major form of casualty. Hemostasis is currently performed using intense heat, electrocautery, lasers, embolization, or application of extreme cold. HIFU offers an alternative as the sonic energy can be focused to a distant point within the body without damage to intervening tissue, allowing non-invasive hemostasis.

Various embodiments of ultrasonic applicators or probes generally include a manipulable transducer, having a power supply and electrical matching circuitry for driving the transducer, and a coupling device for guiding the ultrasonic energy from the face of the transducer to the site of the tissue to be treated. Coupling devices consist generally of a hollow members filled with water. Water provides excellent coupling of acoustic energy into tissue because of the similarity in their acoustic impedances; both media have a characteristic impedance of approximately 1.5 megarayls. However, it has been found that there are disadvantages in the use of the water-filled coupling for medical procedures. At the high intensities at which the device is operated, the water in the coupling device is prone to cavitation; the bubbles produced are disruptive to the ultrasound energy. Thus, degassed water must be used to reduce the chance for cavitation. Furthermore, a water-filled device in a surgical environment is very difficult to sterilize and it must be refilled with sanitary, degassed water each time it is used. If the coupling device ruptures, water leaks out and blood from the patient leaks in, further complicating surgical conditions. Extra tubes and equipment are required to pump and circulate the water within the cone, making for a complicated and cumbersome apparatus difficult to optimize for emergency rescue situations.

In the use of HIFU, another problem is that driving transducers at high voltage generates heat. The frequencies required lead to the need for thin, fragile transducer elements. Thus, a HIFU medical instrument has inherent design problems which can make an HIFU instrument hard to use manually and.where overheating can cause transducer failure.

Thus, there is a need for improved ultrasound-to-tissue coupling devices. A simple, effective coupling device to replace the water-filled coupling devices must be easily sterilized and prepared for use or quickly refittable with a prepackaged, sterile replacement. A solid-state coupling device must additionally resolve the existence of inherent shear modes which complicate and adversely affect the transmission of longitudinal mode ultrasonic energy, the more effective form for most therapeutic type medical procedures. Furthermore, there is a need for improving ultrasonic applicators amenable for use in catheteric medical procedures.

SUMMARY OF THE INVENTION

In one of its basic aspects, the present invention provides a method for producing a therapeutic, high intensity, focused, ultrasonic energy pattern in living tissue. The method includes the steps of: focusing a beam of ultrasound through a solid material such that it converges towards a focal point in the solid material; truncating the solid material behind the focal point; refocusing the beam with a lens at the focal point to provide a predetermined focal region externally of the solid material; and coupling the lens to the living tissue such that the focal region is directed to a target point within the living tissue. More specifically, the method includes generating a sonic wave with a concave transducer;

coupling the transducer to a solid coupler, the coupler having a predetermined geometric apex, wherein the sonic wave is transmitted through the coupler within a predetermined external boundary layer of the coupler; prior to the wave reaching the apex, subjecting the wave to a lens for redirecting the sonic wave; and coupling the lens directly to the living tissue such that the focal region is directed to a target within the living tissue. The method also includes tailoring transducer geometry and coupler geometry and transducer generating frequency to specific therapeutic tasks.

In another basic aspect, the present invention provides a high intensity focused ultrasonic applicator device for performing medical procedures, including: at least one transducer for generating a focused ultrasound beam; mounted to the transducer, a coupler, or applicator, which transmits the beam towards a focal point therein; the coupler is formed of a solid material; and a lens mechanism, located between the transducer and the focal point, for redirecting the beam.

In another basic aspect, the present invention provides a high intensity focused ultrasound medical instrument, including: a handle; mounted to the handle, a housing including a cavity; a transducer having a substantially concave geometry for providing a focused ultrasonic beam from a transducer concave frontside, wherein the transducer is mounted in the housing such that a transducer backside thereof is open to the cavity; and an ultrasound applicator, having an applicator backside having a convex geometry substantially identical to the concave geometry of the transducer; the applicator is nested with the transducer with the transducer concave frontside substantially adjacent the applicator backside; the applicator being of a solid material having a truncated tip such that the tip forms a lens for refocusing the beam; and the handle is adapted for providing a conduit for coupling power and a cooling medium to the cavity.

It is an advantage of the present invention that it provides improved ultrasonic coupling to living tissue.

It is an advantage of the present invention that it provides surgical means for achieving rapid hemostasis in an ultrasonic surgical instrument that can be tailored to access difficult areas.

It is an advantage of the present invention that it provides a practical high intensity focused ultrasound applicator that is easily usable and virtually fool proof in surgery.

It is another advantage of the present invention that is provides a medical applicator of high durability which is easily cleaned and sterilized.

It is another advantage of the present invention that it is adaptable to sterile packaging of quick-fit replacement elements.

It is a further advantage of the present invention that it requires no special maintenance for surgical environments.

It is a further advantage of the present invention that it is easily held and used by the surgeon in cauterizing and treating tissue.

It is still another advantage of the present invention that it is easily manufactured using conventional processes.

It is still another advantage that it provides a surgical tool having a shape that provides a visual pointer towards where the therapeutic energy will be.

It is still another advantage of the present invention that it can incorporate with secondary energy sources, measuring tools, diagnostic or therapy instruments, and the like.

It is yet another advantage that it can be implemented in a portable, battery-powered embodiment for both surgery and emergency trauma remote site use.

It is yet another advantage of the present invention that it can provide rapid treatment to a large tissue surface area.

It is yet another advantage of the present invention that the apparatus can be used in a Doppler ultrasound mode to aid in positioning the apparatus with respect to a hemorrhage site for accurate application of HIFU therapy.

Other objects, features and advantages of the present invention will become apparent upon consideration of the following explanation and the accompanying drawings, in which like reference designations represent like features throughout the drawings.

BRIEF DESCRIPTION OF THE DRAWINGS

FIG. 1 is a perspective view of a hand-held embodiment of an ultrasonic applicator for surgical applications in accordance with the present invention.

FIG. 1A is an exploded detail section of the present invention as shown in FIG. 1.

FIG. 1B is a schematic, cutaway, representation of the present invention as shown in FIG. 1.

FIGS. 2A through 2C are perspective depictions of alternative embodiments of the present invention as shown in FIG. 1.

FIG. 3 shows schematic representations of various embodiments of the present invention as shown in FIGS. 1–1B and 2–2C showing different focal length, converging acoustic energy patterns.

FIG. 4 shows schematic representations of various embodiments of the present invention as shown in FIGS. 1–1B, 2–2C, and 3 showing different focal length, diverging acoustic energy patterns.

FIG. 5 shows a schematic representation of an alternative embodiment to the conical ultrasound applicators of the present invention as shown in FIGS. 1–4.

FIGS. 7A and 7B are illustrations of a computer simulation printout depicting wave propagation using a metallic embodiment cone ultrasonic coupling device in accordance with the present invention as shown in FIGS. 1–1B.

FIGS. 8A, 8B, 8C, and 8D are waveforms related to the simulations as shown in FIGS. 6A, 6B and 7A, 7B.

FIGS. 9A and 9B are schematic representations of another alternative embodiment of the present invention as shown in FIGS. 1–1B, having a waveguide tip.

FIG. 10 is a schematic representation of an alternative embodiment of the present invention having a secondary energy source.

FIGS. 14A and 14B is a schematic representation of an alternative embodiment of the present invention having a secondary energy source applied from an attachment to the coupling device in accordance with the present invention as shown in FIGS. 1–1B.

FIGS. 15A and 15B are schematic representations for a control unit in accordance with the present invention, having a plurality of applicators as shown in FIGS. 2A–2C.

Figure 6A:
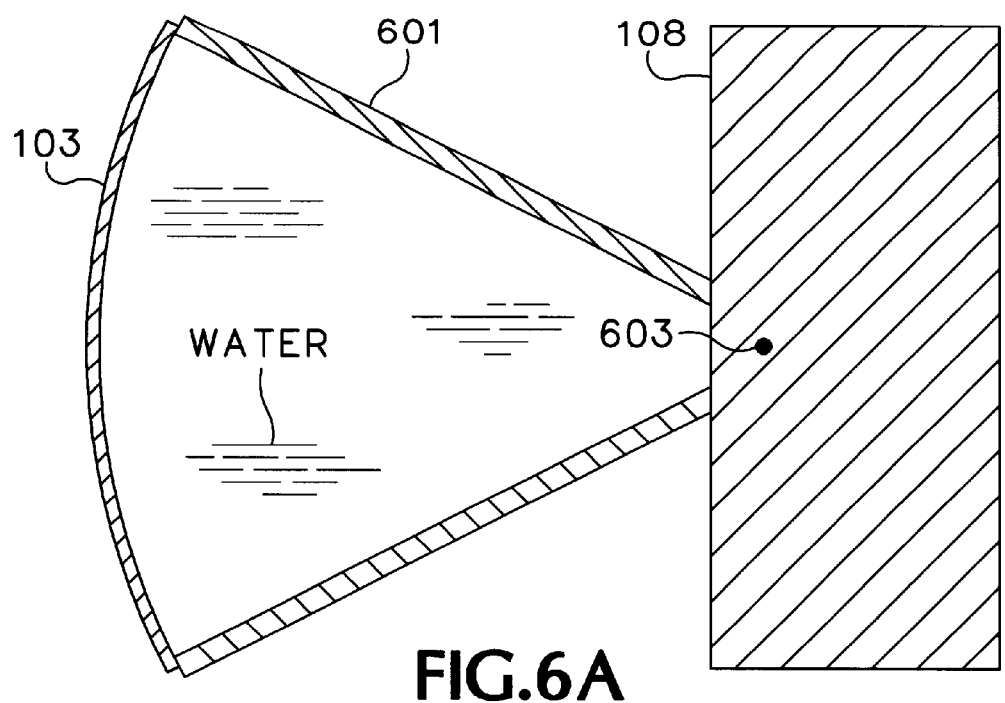
FIGS. 6A and 6B are illustrations of a computer simulation depicting wave propagation through a water-filled cone ultrasonic coupling device into tissue.

The drawings referred to in this specification should be to understood as not being drawn to scale except if specifically noted.

DESCRIPTION OF THE PREFERRED EMBODIMENT

Reference is made now in detail to a specific embodiment of the present invention, which illustrates the best mode presently contemplated by the inventors for practicing the invention. Alternative embodiments are also briefly described as applicable. Subtitles provided hereinafter are for the convenience of the reader; no limitation on the scope of the invention is intended thereby nor should any such limitation be implied therefrom.

General HIFU Medical Instrument

FIG. 1 shows a hand-held embodiment of an ultrasonic medical instrument 100 for medical procedure applications in accordance with the present invention. An ultrasound coupling applicator 101 (also referred to herein as the "semi-cone" because of its geometry, or generically as a "coupling cone") is fabricated of a solid material effectively transmits ultrasonic energy into living tissue, achieving intensities at the focal region that approximate or exceed those obtained by fluid coupling devices. In an exploded perspective view, FIG. 1A shows detail of the headpiece 102 of the ultrasonic medical instrument. A transducer 103 is bonded to the coupling cone 101. A housing 104 receives the transducer 103 and cone 101 pair.

In the preferred embodiment, a very thin, piezoelectric transducer 103 element is directly bonded to the solid cone 101. Because the thickness of an ultrasound piezoelectric transducer 103 element must decrease to produce higher frequencies—namely to a thickness equal to half-wavelength—the element becomes increasingly fragile at the preferred higher frequencies. However, by mounting the piezoelectric element directly to the cone, the cone provides support and thus the ultrasonic medical instrument is more durable and shock resistant. Water-filled devices do not provide this type of mechanical advantage. The backside (left in FIG. 1A) of the transducer 103 is open to air to ensure sonic energy is directed only into the coupling cone 101 and to provide a cooling surface at the backside of the transducer. A cooling medium other than air can be employed.

As seen in FIG. 1, a handle 105 carries conduits or itself forms a conduit; the handle thus provides access to the headpiece 102 for, e.g., the electrical wires 106 connected to a control unit (described in more detail below). The ultrasonic medical instrument in general is implemented with materials and a geometry such that it can be easily cleaned and gas sterilized; preferably medical instruments are autoclavable. FIG. 1B depicts the ultrasonic medical instrument schematically in which a transducer-backing cavity 107 in the headpiece 102 is demonstrated. Within the handle 105 is a cooling channel 109 providing air, or other cooling medium into the cavity 107 behind the transducer 103. A separate electrical wire conduit 110 is also shown. Box 108 represents the tissue to be treated.

As seen in FIGS. 1A and 1B, the large end of the coupling cone 101 is convex so that it fits up against the bowl of the convex transducer 103; the cone tapers following the outline of the focused acoustic rays from the edge of the transducer. The tip of the cone 101 is selectively truncated as explained hereinafter in further detail.

The ultrasound applicator 101 is fabricated of a solid material with low acoustic attenuation. Materials suitable for medical application include ceramic, glass, fused quartz, and metal, with a preference for ceramic as ceramic piezoelectric transducers are commonly used in medical ultrasound. Thus, a ceramic applicator 101 offers excellent acoustic matching to a ceramic-type transducer 103 without the need for intervening matching layers. Steel, silver, aluminum, and zinc also offer good acoustic matching properties and will be less expensive than ceramic or glass. A glass applicator 101, such as of crown glass, offers the least suitable impedance matching option, but offers the possibility of a see-through device which would be advantageous during a surgical procedure.

The outer boundary of the solid coupling cone 101 is designed to be wider than the taper of the sonic beam pattern imposed by the concave transducer 103. This minimizes reflections and mode conversions at the boundaries.

Altering the handle orientation provides implementations suited to different surgical needs. FIG. 2A depicts an ultrasonic ultrasonic medical instrument in a pencil-handled configuration. FIG. 2B demonstrates ultrasonic ultrasonic medical instrument in a tilt-handled configuration. FIG. 2C illustrates the ultrasonic medical instrument as shown in FIG. 1 with an actuator switch 201 added.

As demonstrated in FIGS. 1 through 1B, the applicator tip is shaped. That is, the solid cone 101 is truncated before the actual geometric conical point. Turning also to FIG. 3, the tip 301 of the actuator 101 is formed as a spherically concave surface substantially similar in radius of curvature to the transducer 103 (FIGS. 1A–1B). The resulting concave tip 301 acts as an acoustic lens whereby very high acoustic intensities can be generated at the focal region of this applicator lens-tip. Alternatively to grinding a concave lens into a lens-tip 301, a Fresnel lens using a material, such as rubber, with an acoustic impedance lower than that of the tissue to be treated can be bonded to the cone tip to improve sonic focusing. As demonstrated by the differently depicted shapes, by altering the radius of curvature of the transducer or the applicator lens-tip 301, different focal lengths, "Lf," reaching different depths from the tip into the tissue, are achieved. Thus, either the diameter of the transducer 103 or the dimensions of the applicator 101 may be altered to produce a variety of implementations. The gain in intensity of the ultrasound generated by the transducer is equal to the surface area of the transducer element divided by the surface area of the truncated tip. Absorption in the tissue is a direct function of frequency; i.e., the higher the frequency the faster the absorption. Thus, a specific implementation can be tailored by transducer and cone geometry and selected transducer frequency.

FIG. 4 illustrates convex cone tip 401 for producing a dispersing of the acoustic energy. This embodiment would be useful for treating the immediately adjacent tissue surface rather than a predetermined depth with the tissue as with the embodiments of FIG. 3. This will allow a higher intensity dispersion over the larger aperture. The convex tip 401 also facilitates movement over the tissue surface, particulary useful in treating open wounds.

FIG. 5 depicts an applicator 101 having wedge-shape and a tip 501 for inducing an ultrasound energy field having a very large cross-sectional area. However, it should be recognized that energy concentrating gain is lost when going from a transducer with a spherical surface to the cylindrical surface 503; higher frequency energy may be needed to compensate. This shape can be useful in cautery "painting" a large tissue surface very quickly, rapidly treating large traumatized tissue areas.

FIGS. 6 and 7 and are computer simulations comparing a prior art ultrasound device and the present invention. The simulations were modeled for a 5 MHZ transducer and all wavelength measurements described below are at this frequency. It has been found that ultrasonic frequencies in the range of approximately 2–10 MHZ are preferred in HIFU medical procedures, although a range of 0.5 to 100 MHZ may be used for specific implementations. The resolution of the transducer increases with increasing frequency, thus allowing smaller effective focal region volumes. Higher frequency energy is absorbed more readily and can produce faster cauterization, but attenuates rapidly and thus has a short range of effectiveness. Thus, operating frequencies are chosen based upon the desired treatment depth, transducer and focused-beam geometries. The transducer diameter must be large enough to produce a power level necessary for cautery—an intensity on the order of 1550 W/cm$^2$, yet small enough for the manufacture of a practicable surgical instrument. A range of approximately 1000–3000 W/cm$^2$ is preferable.

Figure 8A:
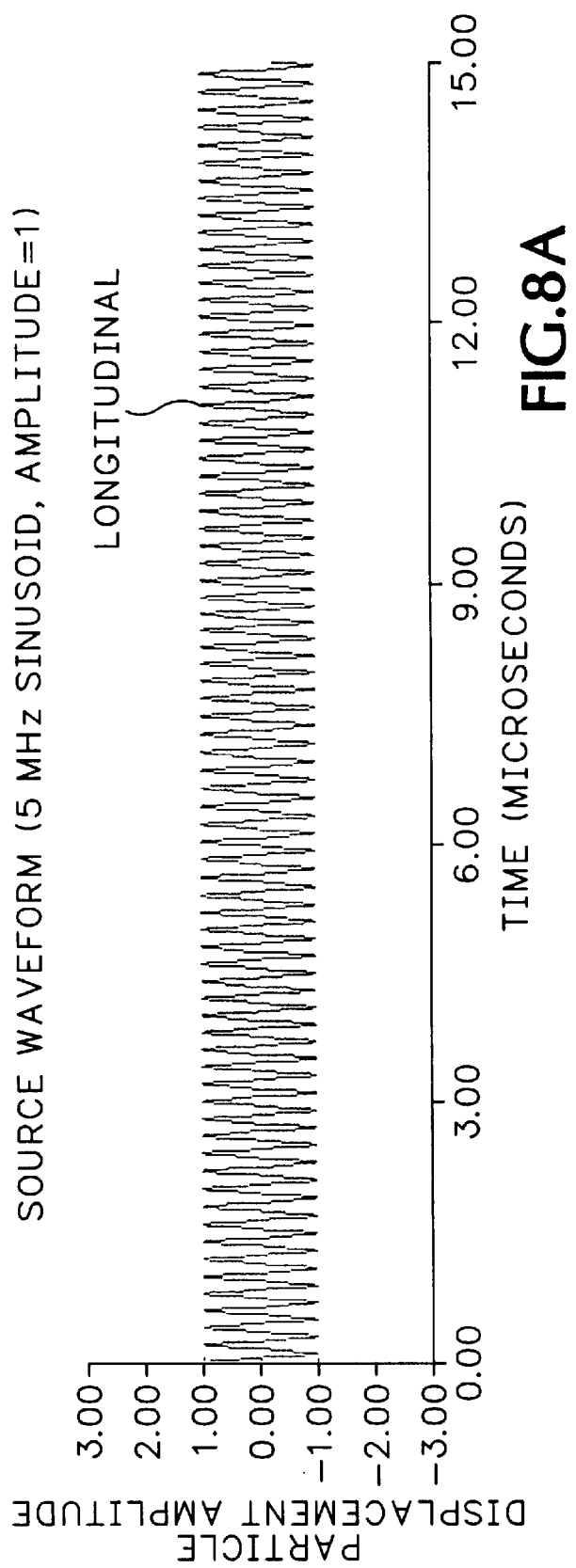

FIG. 6A shows the two-dimensional model of a water-filled cone applicator 601. The model is of a transducer 103 that consists of a spherically concave half-wavelength thick, zirconate titanate ceramic layer, known as PZT-4, to which a quarter-wavelength thick matching-layer has been added. The transducer is 33 mm in diameter with a radius of curvature of 35 mm and a thickness of 0.46 mm (half the acoustic wavelength in PZT-4 at 5 MHZ). The entire model image is 50 mm×33 mm. The prior art coupling device is a hollow, 2.5 mm thick, Plexiglas™, cone filled with water (material properties used for water at 25° C.). The "Tissue" portion of the model was given the material properties of fresh human blood. All white areas and areas outside the boundaries of the image are assumed to have the properties of air. Excitation of the transducer is achieved by placing sine wave source excitations in a continuous line down the center of the PZT-4 thickness. The sine wave is shown in FIG. 8A. The source produces a particle displacement in front and in back of this line. As this displacement hits the boundaries of the ceramic layer, it is essentially expanding and compressing the boundaries. This is similar to the way a real piezoelectric transducer is expanded and compressed by electrical stimulation.

The simulations were run for a time sufficiently long enough to allow the propagating wave front to reach a point several centimeters beyond the expected focal region in the Tissue (this time will vary depending on the material used as the coupling cone). Note that due to limitations in the software used, the models represent two-dimensional cross-sections of the actual device. Also note that temperature changes and other non-linear effects were not accounted for in o this simulation.

Figure 6B:
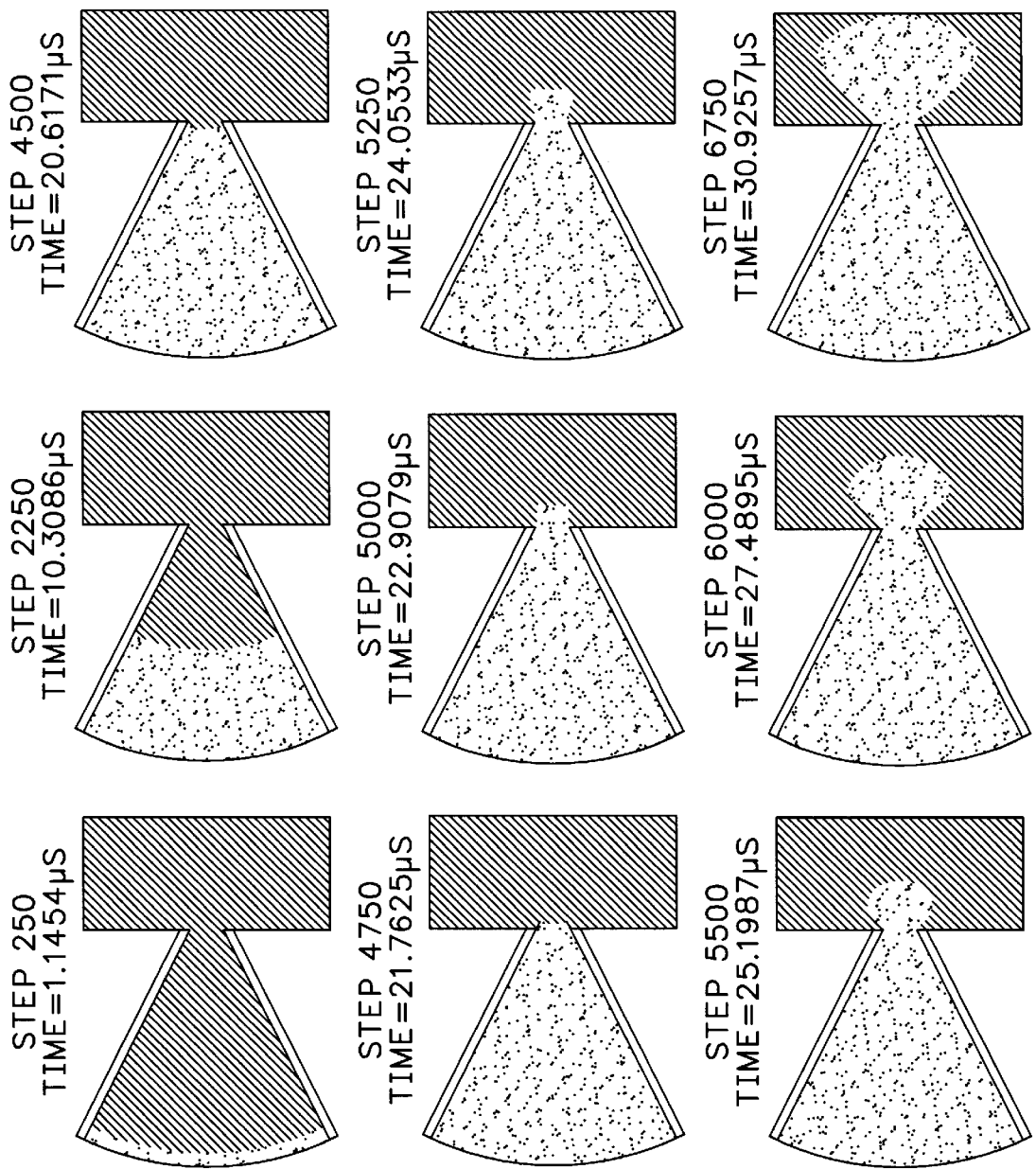

The location of a Sampling Point 603 records the waveform as it propagated through the FIG. 6A model at x=35 mm, where far left of the model image is at x=0 with values increasing to the right (for reference, the water-facing surface of the transducer at its vertical center point is located at x=3 mm). Due to the curvature of the transducer, the focal region is expected to center on the sampling point at x=38 mm. FIG. 6B is series of nine gray-scale images generated by the model of FIG. 6A and are "snapshots" showing the ultrasonic wave propagation captured while the simulation was running; the simulation "Step" and "Time are shown above each. The propagating wave is shown in white in order to contrast the propagating wave more effectively. Brighter areas indicate areas of larger amplitude (i.e. larger particle displacement). The image at FIG. 6B, Step 5250, Time=24.0533 μs, is the approximate time at which the focal region within the tissue 108 is reached by the wave front.

Figure 7A:
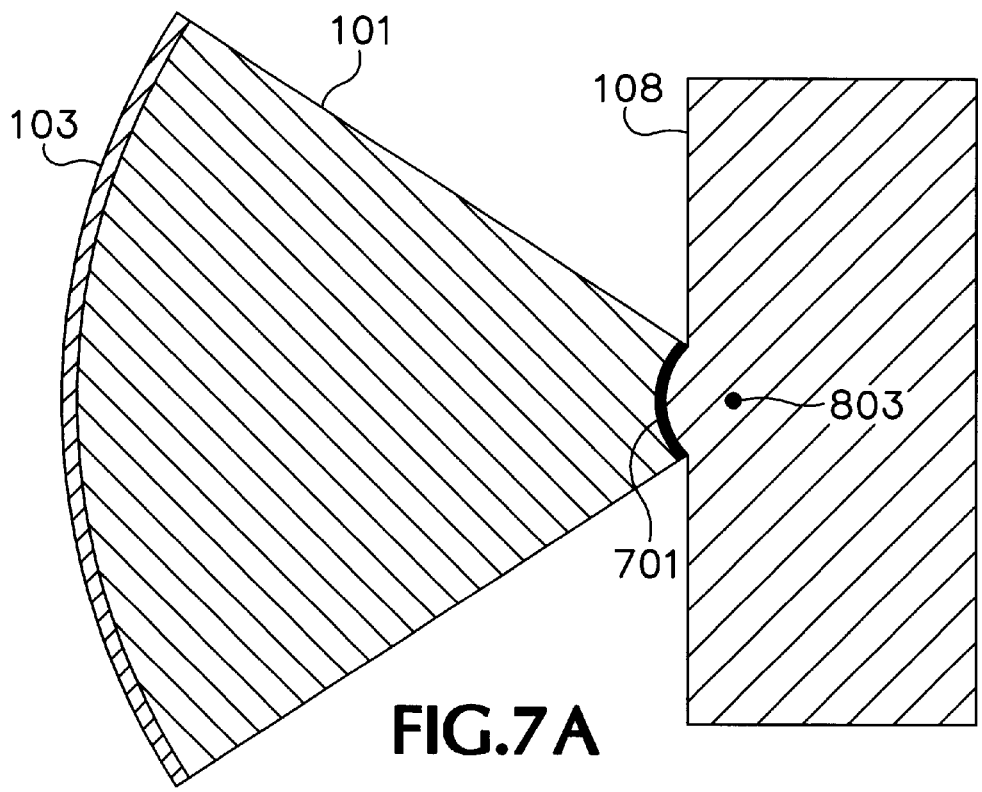

FIG. 7A shows similar images for a computer models embodiment of the present invention using a simulated solid semi-cone 101 (see FIGS. 1–1B). Aluminum was modeled as it is preferable to other metals because of its very low relative acoustic loss., having an acoustic impedance of $Z_{a1}$=17.3 megarayls. The transducer 103 modeling characteristics are the same as the one in FIG. 6A, with the exception of the addition of a ¼-wavelength matching-layer 701 at the cone 101 to Tissue 108 interface. That is, in the modeling of the present invention, there is no matching-layer between the transducer 103 and applicator 101. Instead, however, a matching-layer 701 appears at the aluminum cone tip. That is, in this alternative embodiment of the present invention, in order to improve acoustic coupling between the applicator 101 and the tissue an appropriate quarter-wavelength matching-layer 701 improves transmission into the Tissue 108. Materials that are suitable for apex matching-layer 701 are dependent on the cone itself; for this simulation, the materials have, having a specific acoustic impedance of 5.58 Mrayls for longitudinal waves, 3.1 Mrayls for shear waves, a velocity of 3100 m/sec for longitudinal waves, a velocity of 1720 m/sec for shear waves, and a density of 1800 Kg/m$^3$. Some examples for commercial matching layer materials are DER-322 epoxy, silver-epoxy, Plexiglas, crown glass, or aluminum, or known manner composites. Note also, that in another alternative embodiment, an acoustic matching layer also can be used as in the prior art to between the transducer element 103 and the cone 101 if required to overcome an acoustic mismatch; however it is preferable that both the transducer and cone be ceramic and fit together so that maximum energy is directly transferred from the transducer into the applicator.

A 0.025 mm (~0.001") layer of epoxy is included between the aluminum-ceramic interface to account for the necessary bonding agent. A 6.35 mm (~0.25") flat region is modeled at the large diameter of the aluminum part. A Sampling Point 803 was used to record the waveform as it propagates is located at x=34.2 mm. As in FIG. 6A, the surface of the transducer at its vertical center point is located at x=3 mm. Due to the curved surface at the probe's tip, the focal region is expected to center on the sampling point at x=37 mm.

For comparison with FIG. 6B, nine gray-scale images showing the propagating wave are included for the FIG. 7A model in FIG. 7B. Because the wavelength in aluminum is about four times larger than in water, the periodic nature of the propagating wave is more clearly seen by the dark and light bands of the wave. Within the wave, white areas indicate maxima and minima of the waveform while black areas indicate areas where the waveform has an amplitude of zero. The image shown at Step 1900, Time=7.6233 μs shows the approximate time at which the wave front has reached the focal region. Thus, in this modeling, the present invention achieves focal energy more than three times faster than the prior art model.

Figure 8C:
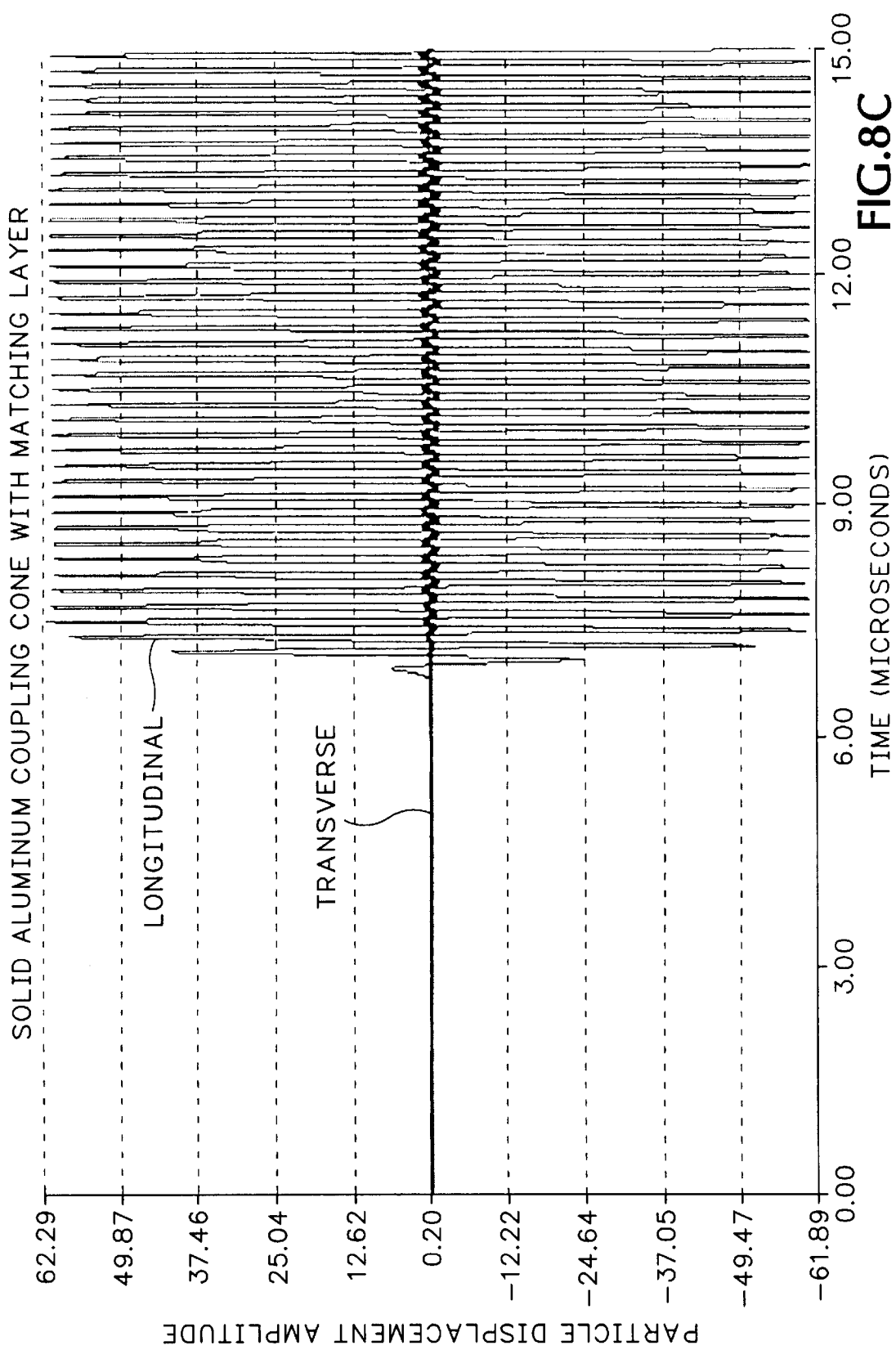
Figure 8D:
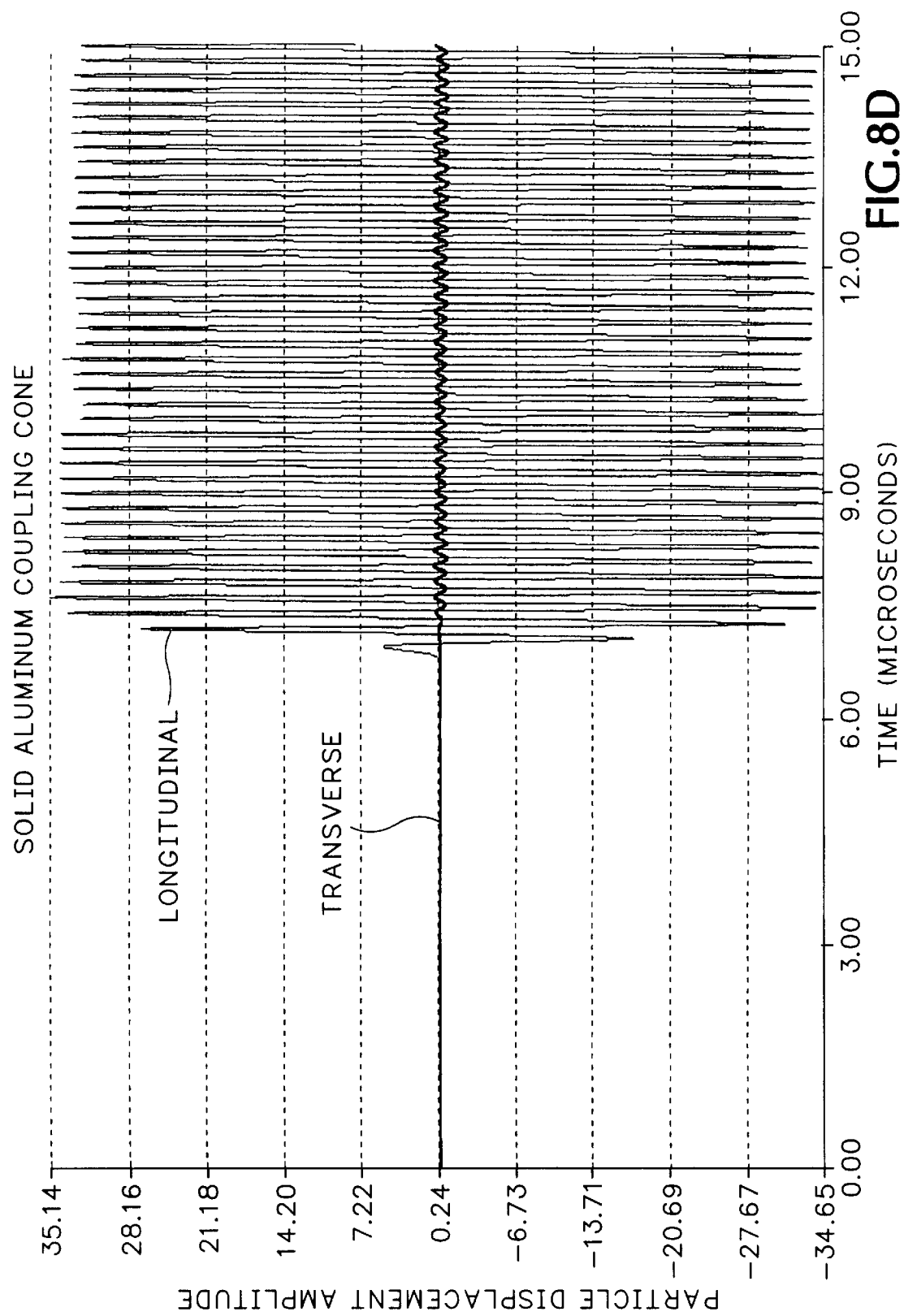

FIG. 8A shows the Source Input Waveform used in each simulation (a continuous sinusoid). FIGS. 8B and 8C are comparisons of the received waveforms at the sampling points from the models of FIGS. 6A and 7A, respectively. All waveforms represent particle displacement. The units are arbitrary, since they are relative to the source waveform, which is normalized to an amplitude of 1. Each sampling point produces a curve in a different line form, as explained in the legend to the right of the received waveform graph. In the title for each curve, the number represents the x-location of the sampling point, relative to the far left of the image. FIG. 8B for the water-filled plastic coupling cone of FIG. 6A shows the waveform that arrives at the point in the tissue at x=35 mm; the average steady state peak particle displacement value is approximately 52. The longitudinal wave is much larger than the shear wave with a peak value of less than 1. FIG. 8C shows the waveform at x=34.2 mm for the solid coupling cone model with the ¼-wavelength matching layer of FIG. 7A. The average steady state peak particle displacement is 60, about 1.15 times larger than for the water-filled plastic coupling cone model. FIG. 8D shows computer simulated results for the present invention as shown in FIGS. 1–1B, that is, a solid coupling cone without a matching layer. The average steady state peak particle displacement is 34, about 0.65 times the value of the water-filled plastic coupling cone model. In commercial implementations, an increased input power may be required to drive the solid cone coupling device.

From these graphs, it can be seen that the coupling cone can be manufactured in such a way that it produces greater particle displacements at the focal region than the water-filled coupling cone.

Alternative Embodiments

FIGS. 9A and 9B depict an alternative embodiment which provides a mechanism 901 for extending the focal region of the applicator 101 to a distal target within the living tissue. This embodiment is thus adapted for endoscopic medical procedures where the only other way to provide therapy may be through invasive surgery. This embodiment is described for generally coupling the ultrasonic energy through a waveguide which has a diameter much smaller than the transducer. The coupling device maybe flexible, stiff, tapered, or composed of multi-structures.

The transducer 103 element and coupling cone 101 are shown similar to the rest of the previously described embodiments. A waveguide 903 is mechanically held to the cone 101 by a nut and thread mechanism 905, or a quick-disconnect mechanism such as a bayonet lock device. The surface of the cone 101 where it mates to the waveguide 903 and the surface of the waveguide which mates to the cone are generally polished to be very smooth to facilitate the ultrasound coupling. A gel, liquid, powder, or thin, soft metal may be imposed between the cone 101 and the waveguide 903 before attaching to promote the coupling. Other types of matching such as a ½-wavelength of intermediate layer may be used The truncation of the cone-tip 301, 401, 501 (FIGS. 3–5) for mating to the waveguide 903 is chosen at a distance from the spherical transducer element 103 where the cross-section of the beam matches or is slightly smaller than the coupling region of the waveguide. The spherical concave surface of the transducer 103 operates through the cone 101 to focus energy on the waveguide 903 surface which is much smaller than the transducer surface. Thus, it can also will provide a collecting means of receiving energy propagating back through the waveguide 903 and for which the ultrasonic energy needs to be applied to a transducer and converted to an electrical signal for processing, such as for Doppler imaging of the target area. As such, this remote treatment instrument may be used for both transmission and reception if desired in specific applications. In alternate embodiments (not shown), the waveguide 903 maybe permanently attached to the cone 101 by welding, soldering, gluing, or other means of fixation.

Other alternative embodiments, having instrument guidance features or secondary energy applicators are shown in FIGS. 10, 11, 12, and 13. In these embodiments, secondary energy sources are combined with the ultrasonic medical instrument and applicator 101.

FIG. 10 has an optical channel 1001 through the cone 101 and transducer 103. A laser diode 1003 is mounted behind the channel 1001 for connection to a power source through the instrumenthandle 104. The diode laser light beam is projected through the optical channel 1001, ultimately illuminating the tissue 108. Thus, a spot of light is projected by the ultrasonic medical instrument to a center of focus for targeting the ultrasound energy. A laser diode electrical connection conduit 1005 passes through the handle 104 for holding the electrical wire 1007 for the laser diode 1003. Such laser diodes are commercially available, such as model 0220-960 by Coherent Instrument Division, Auburn, Calif.

Figure 11:
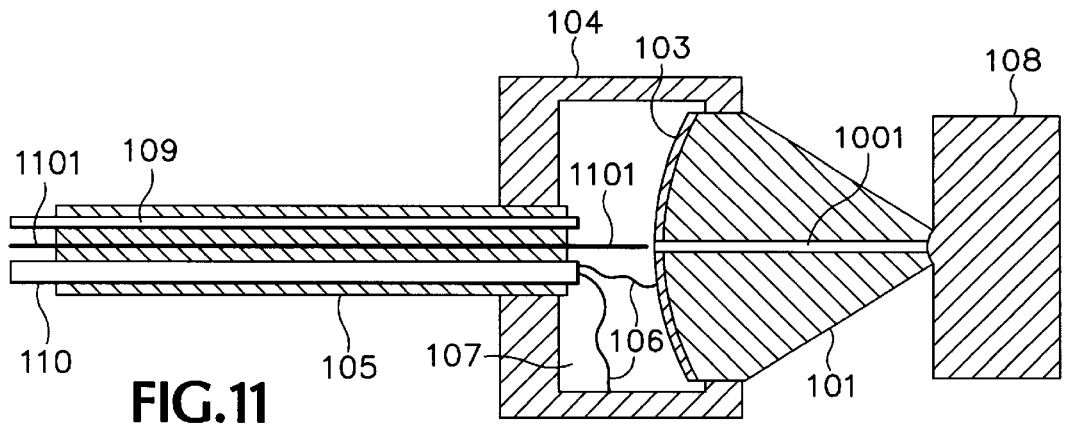
FIG. 11 is a schematic representation of an alternative embodiment of the present invention having a secondary energy source.

FIG. 11 similarly has a coupling cone 101 with an optical channel 1001. A fiber optic cable 1101 is passed through the handle 104 and the optical fiber aligned to emit a beam of light through the optical channel for illuminating the target tissue at the focal zone of the applicator 101. Note that a therapeutic laser can also be combined with the present invention in this same manner by coupling through such a fiber optic cable. It is also possible to use the fiber optics for automatic colorimetric analysis of the treated area during treatment in order to provide feedback as to the status of the treatment.

Figure 12:
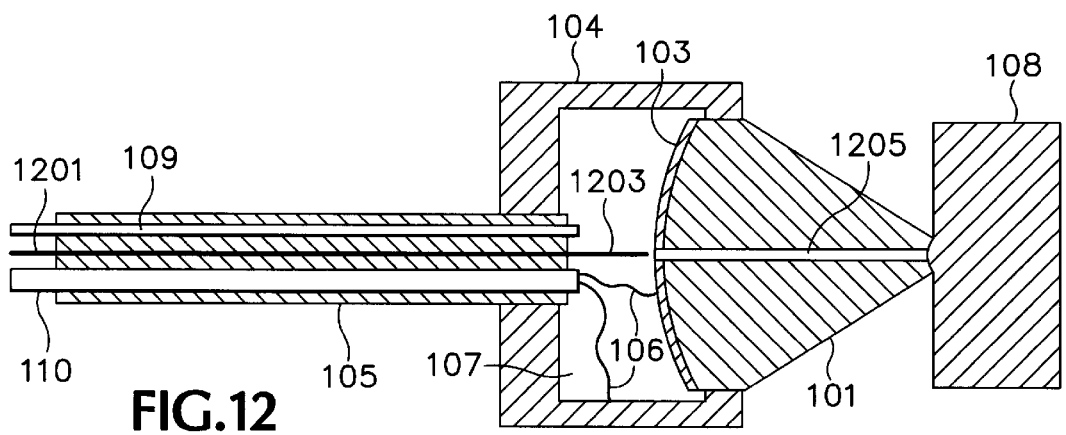
FIG. 12 is a schematic representation of an alternative embodiment of the present invention having a secondary energy source.

FIG. 12 is an embodiment in which a high velocity, fluid-jet, secondary energy source is provided. A fluid conduit 1201 passes through the handle 104. The nozzle end 1203 of the fluid conduit 1201 is aligned with a fluid channel 1205 through the center axis of the ultrasound coupling cone 101.

Figure 13:
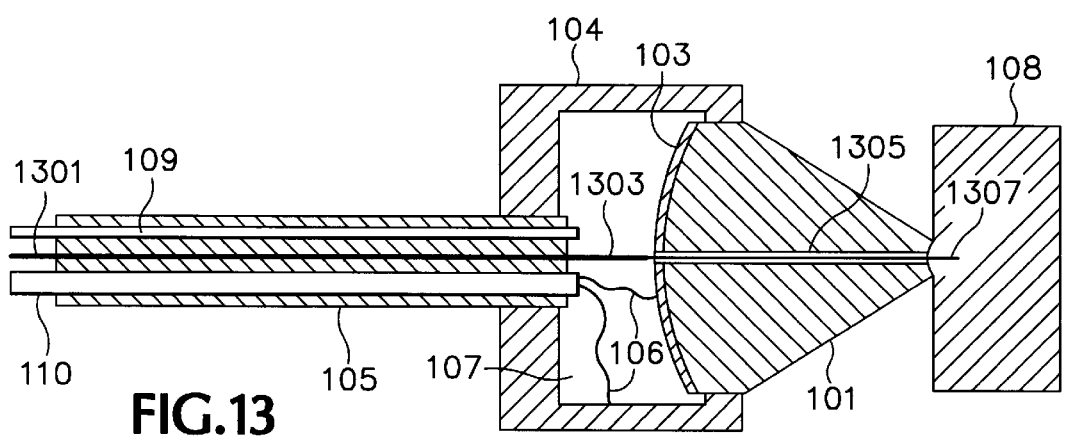
FIG. 13 is a schematic representation of an alternative embodiment of the present invention having a secondary energy source.

FIG. 13 is another embodiment in which a electrical surgery probe tip is provided. A known-in-the-art RF electrosurgery probe 1301 passes through the handle 104. Within the housing 104, a socket end 1303 is positioned adjacent a RF-wire channel 1305 that passes through the axis of the cone 101. A replaceable RF tip 1307 can be inserted through the channel 1301 into the socket end 1303 and then protrudes from the cone-tip into the tissue 108.

FIGS. 14A and 14B illustrates how a secondary energy can be transmitted through a similar guide 1401 to those referenced with respect to FIGS. 10–13, but adjacently mounted to the ultrasound coupling cone 101. A tip adapter 1403 can provide appropriate mounting and tissue coupling features for the specific secondary energy employed and, preferably be constructed such that simultaneous use of ultrasonic therapy can be administered.

Thus, it can be recognized that these alternative embodiments may be used both for a secondary energy application or for feedback.

Bi-directional light energy may be used to sense the color or fluorescence of the tissue. A particular color change may indicate the probe is over a tissue that needs to be treated and thus used to automatically active the application of therapeutic energy (for example a darker region may indicate a tumor). It may sense a change in color while therapeutic energy is applied (for example tissue turning from red to gray) indicated enough therapy has been applied and thus to shut off or turn down the energy being applied at that point.

Micro-endoscope technology might be incorporated through the channel providing a visual image of the tissue at the tip of the applicator. This would allow the user to visualize the tissue at the tip. This may be very useful with applicators such as in FIG. 3 where there is a long applicator for reaching deep into crevices or possibly as shown FIG. 9 where wave guides may be used for coupling energy over relatively long distances.

Electrical signals may be used in a thermocouple or thermistor mounted near the tip to sense temperature at the tip. Alternatively, electrical current (e.g. at 100 KHz) to measure the tissue electrical impedance can allow detecting when tissue is in contact—turning on and off the unit automatically when it is in contact and not in contact, respectively, based on the impedance change. Further, the tissue electrical impedance will change with temperature. Therefore, as the ultrasound energy heats it up the electrical impedance change can be used to indicate therapeutic action is being achieved and therefore provide feedback to the user or directly to the unit to control the energy delivery. In this mode, a single wire with an electrode at the tip may act as monopolar impedance electrode measuring impedance against a common electrode located elsewhere on the body. Monopolar impedance measurement methods are well known in the state of the art. The cone may be the common electrode in some cases allowing very local impedance measurements. Two wires may be employed alternatively in bi-polar mode for localized measurements. The metallic cone itself with out the use of a channel can also be used a monopolar electrode for the same purposes.

Acoustic devices may be incorporated through the channel to detect acoustic energy such as broad band noise produced by cavitation. This information may be used to shut down therapeutic energy if cavitation is undesirable or to increase energy if cavitation is not detected but is desired as part of the therapy. An alternative frequency and an alternative form (i.e. pulsed differently or continuous) may be used to receive or transmit to obtain information useful for guiding therapy. For example, a Doppler ultrasound element or elements with appropriate connecting wires may be placed in the channel. This may be used to provide Doppler signals of blood flow to guide therapeutic action that are less noisy than if the concave transducer attached to the cone is used. Alternatively a miniature ultrasound array may be used there to provide local ultrasound imaging of the region and thus guidance. An example, in the state of the art in miniature ultrasound arrays are ones that have been incorporated into intravascular catheters.

A miniature pressure sensor or fluid filled tube connected to a pressure sensor may be incorporated into the channel. This provides a measure of blood pressure that may be pressing against the cone and thus guide locating a breach in the vessel wall. It also may give an indicative measure of radiation pressure being produced by the therapeutic energy and therefore provide a feedback for closed loop control of applied therapeutic energy.

Controller

Figure 15B:
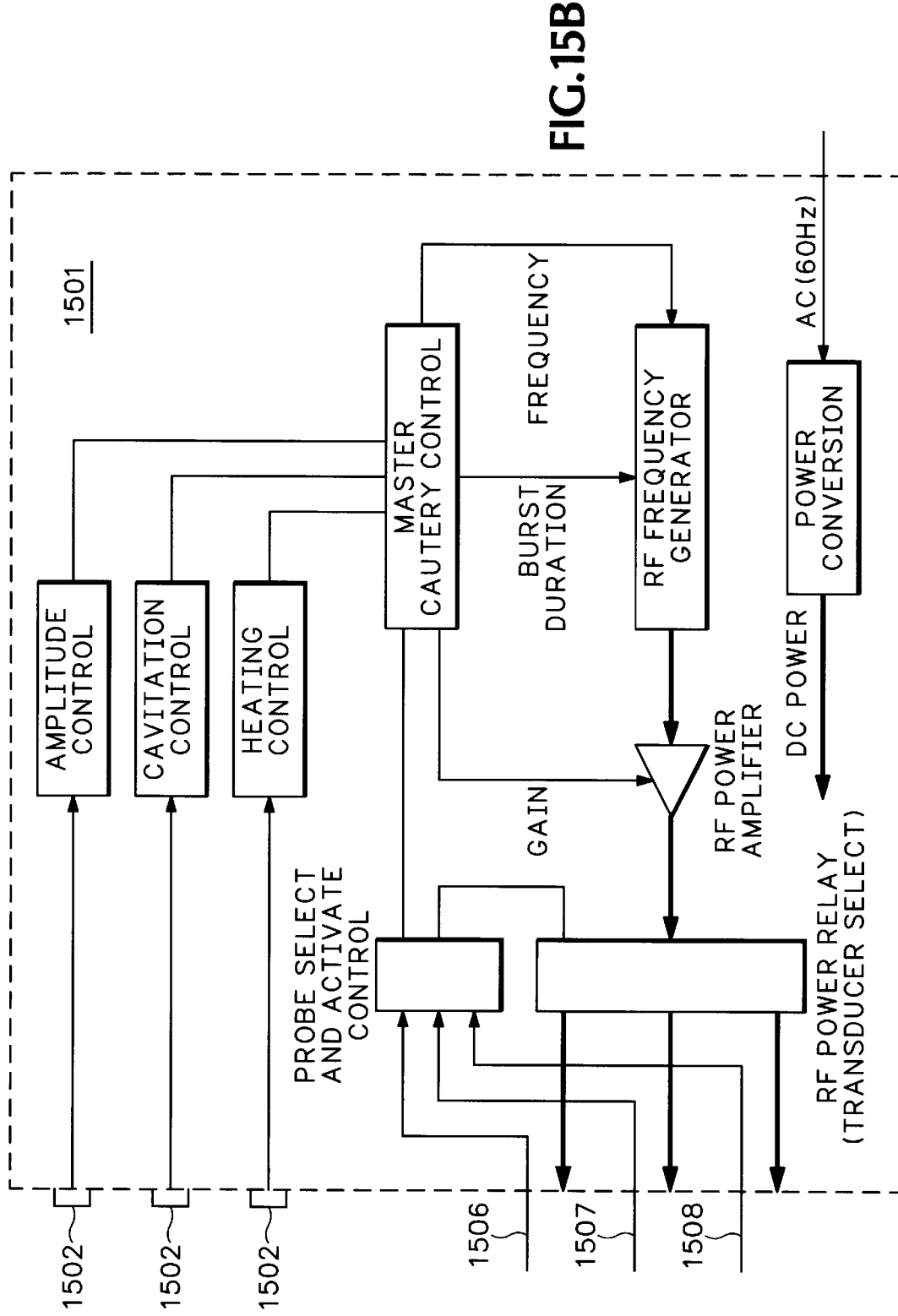

FIGS. 15A and 15B illustrate a control system for use in conjunction with the ultrasonic ultrasonic medical instrument 100. A surgical unit 1501 is provided with panel controls 1502 for use by medical personnel, such as a surgeon. Three, or any other suitable number, different style probes 1503, 1504, 1505 for specific surgical applications are connected to the unit 1501 by appropriate cables 1506, 1507, 1508, respectively. The surgeon picks the specific applicator, or probe, needed for the current task, brings it to the treatment target site, and activates it by depressing the activation switch 201 on a selected probe 1503, 1504, or 1505 and making adjustments of the appropriate function from the panel controls 1502.

FIG. 15B is an block diagram of the surgical unit 1501. Each probe when connected to the unit 1501 and activated by the surgeon provides a Probe Select and Activate Control signal. The Probe Select and Activate Control signal informs a Master Cautery Control to apply the (frequency, amplitude, burst duration, and the like as would be known in the art) for the currently signaling probe to the RF Frequency Generator. Master Cautery Control is adjustable from the front panel controls 1502, such as for "Amplitude," "Heat" levels, and "Cavitation" power The RF Frequency Generator develops the preselected control needed and provides the signal to the RF Power Amplifier. The RF Power Amplifier output is routed by RF Power Relays to the appropriate probe.

The foregoing description of the preferred embodiment of the present invention has been presented for purposes of illustration and description. It is not intended to be exhaustive or to limit the invention to the precise form or to exemplary embodiments disclosed. Obviously, many modifications and variations will be apparent to practitioners skilled in this art. Similarly, any process steps described might be interchangeable with other steps in order to achieve the same result. The embodiment was chosen and described in order to best explain the principles of the invention and its best mode practical application, thereby to enable others skilled in the art to understand the invention for various embodiments and with various modifications as are suited to the particular use or implementation contemplated. It is intended that the scope of the invention be defined by the claims appended hereto and their equivalents. Reference to an element in the singular is not intended to mean "one and only one" unless explicitly so state, but rather means "one or more." No element, component, nor method step in the present disclosure is intended to be dedicated to the public regardless of whether the element, component, or method step is explicitly recited in the claims. No claim element herein is to be construed under the provisions of 35 U.S.C. Sec. 112, sixth paragraph, unless the element is expressly recited using the phrase "means for . . . "

What is claimed is:

1. A method for producing a therapeutic, high intensity, focused, ultrasonic energy pattern in living tissue, comprising the steps of:

focusing a beam of ultrasound through a solid material such that it converges towards a focal point in the solid material;

truncating the solid material behind the focal point;

refocusing the beam with a lens at the focal point to provide a predetermined focal region externally of the solid material; and coupling the lens to the living tissue such that the focal region is directed to a target point within the living tissue.

2. The method as set forth in claim 1, further comprising:

generating a sonic wave with a concave transducer;

coupling the transducer to a solid coupler, the coupler having a predetermined geometric apex, wherein the sonic wave is transmitted through the coupler within a predetermined external boundary layer of the coupler;

prior to the wave reaching the apex, subjecting the wave to a lens means for redirecting the sonic wave; and coupling the lens means directly to the living tissue such that the focal region is directed to a target within the living tissue.

3. The method as set forth in claim 2, comprising the steps of:

providing the transducer and coupler with an associated geometric construction and a transducer ultrasound generating frequency tuned for specific respectively predetermined therapeutic tasks.

4. A high intensity focused ultrasonic device for performing therapeutic medical procedures, comprising:

transducing means for generating a focused ultrasound beam;

mounted to the transducing means, coupling means for transmitting the beam toward a focal point within the coupling means, wherein the coupling means is formed of a solid material; and a lens means for redirecting the beam, wherein the lens means is located between the transducing means and the focal point such that the focal point is external to the solid material.

5. The device as set forth in claim 4, comprising:

the transducing means is a concave piezoelectric element having a thickness approximately equal to one-half wavelength of a predetermined ultrasound beam frequency generated thereby.

6. The device as set forth in claim 5, comprising:

the coupling means is a semi-cone of a solid material having low acoustic attenuation.

7. The device as set forth in claim 6, comprising:

the semi-cone having a rear geometry for mounting the piezoelectric element directly to the semi-cone such that the semi-cone provides mechanical support for the piezoelectric element.

8. The device as set forth in claim 6, comprising:

the semi-cone is formed of a solid material selected from a group of materials including ceramic, glass, fused quartz, or metal.

9. The device as set forth in claim 6, comprising:

the semi-cone has an outer boundary wider than a taper of the sonic beam pattern imposed by the concave piezoelectric element wherein beam reflections and mode conversions at the boundary are minimized.

10. The device as set forth in claim 6, comprising:

the lens means is a selectively truncated tip of the semi-cone.

11. The device as set forth in claim 4, comprising:

mounted to the lens means, an acoustic impedance matching means for coupling the lens to a load representative of specific living tissue.

12. The device as set forth in claim 11, comprising:

the matching means is a quarter-wavelength matching-layer of a material selected from a group including: DER-322 epoxy, silver-epoxy, Plexiglas, crown glass, aluminum or composites thereof.

13. The device as set forth in claim 4, comprising:

the transducing means has a backside open to air such that sonic energy generated by the transducing means is directed only into the coupling means and the backside provides a cooling surface at the backside of the transducing means.

14. The device as set forth in claim 4, comprising:

the lens means is a truncated tip of a predetermined geometric shape associated with the coupling means, the tip having a predetermined geometry for either refocusing the ultrasound beam to a predetermined focal length or for spreading the ultrasound beam immediately adjacent the tip.

* * * * *